(12) United States Patent
Bashkirov et al.

(10) Patent No.: US 8,551,697 B1
(45) Date of Patent: Oct. 8, 2013

(54) ELECTROCHEMICAL POLYNUCLEOTIDE DETECTION COMPRISING LIGATION

(75) Inventors: Vladimir I. Bashkirov, Davis, CA (US); Konrad Faulstich, Salem-Neufrach (DE)

(73) Assignee: Applied Biosystems, LLC, Carlsbad, CA (US)

(*) Notice: Subject to any disclaimer, the term of this patent is extended or adjusted under 35 U.S.C. 154(b) by 189 days.

(21) Appl. No.: 11/609,111

(22) Filed: Dec. 11, 2006

Related U.S. Application Data

(60) Provisional application No. 60/748,998, filed on Dec. 9, 2005.

(51) Int. Cl.
| | | |
|---|---|---|
| C12Q 1/68 | (2006.01) | |
| C12P 19/36 | (2006.01) | |
| C12P 19/34 | (2006.01) | |
| C07H 21/02 | (2006.01) | |
| C07H 21/04 | (2006.01) | |

(52) U.S. Cl.
USPC ......... 435/6.1; 435/6.12; 435/91.1; 435/91.2; 435/91.52; 536/23.1; 536/24.3

(58) Field of Classification Search
USPC .............. 435/6.1, 6.12, 91.1, 91.2, 91.52; 536/23.1, 24.3
See application file for complete search history.

(56) References Cited

U.S. PATENT DOCUMENTS

| 5,942,609 A * | 8/1999 | Hunkapiller et al. ....... 536/25.3 |
| 6,686,150 B1 * | 2/2004 | Blackburn et al. ............... 435/6 |
| 2003/0207295 A1 * | 11/2003 | Gunderson et al. .............. 435/6 |
| 2004/0214176 A1 * | 10/2004 | Osborne et al. .................. 435/6 |
| 2004/0259106 A1 * | 12/2004 | Gunderson et al. .............. 435/6 |

FOREIGN PATENT DOCUMENTS

| WO | 97/08183 | | 3/1997 |
| WO | WO 97/08183 | * | 3/1997 |
| WO | 03/074731 | | 9/2003 |
| WO | WO03074731 | * | 9/2003 |
| WO | 2005/010199 | | 2/2005 |
| WO | WO 2005/010199 | * | 2/2005 |

OTHER PUBLICATIONS

Yu et al, Electronic Detection of Single-Base Mismatches in DNA with Ferrocene-Modified Probes, 2001, J. Am. Chem. Soc., 123, 11155-11161.*

Yu, et al., "Electronic Detection of Single-Base Mismatches in Dna with Ferrocene-Modified Probes", Journal of the American Chemical Society, vol. 123, Issue 45, Nov. 14, 2001, 11155-11161.

* cited by examiner

*Primary Examiner* — Narayan Bhat

(57) ABSTRACT

Disclosed, for example, are methods comprising cleaving an uncleaved probe to form a cleaved oligonucleotide flap, forming a hybridization complex between the cleaved oligonucleotide flap, a bridging oligonucleotide, and a capture oligonucleotide that is immobilized on a surface, such that the oligonucleotide flap and the capture oligonucleotide are hybridized to immediately adjacent, complementary regions of the bridging oligonucleotide, ligating the oligonucleotide flap to the capture oligonucleotide to form an immobilized ligation product, and detecting the ligation product.

3 Claims, 2 Drawing Sheets

Figure 1:
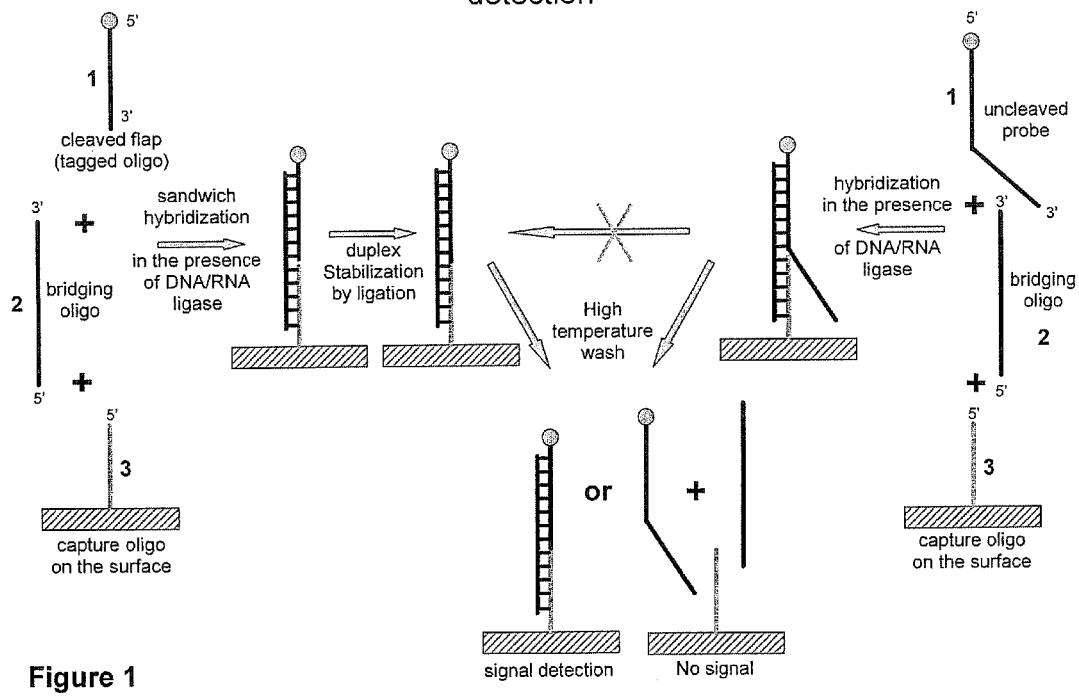

Ligase-mediated capture of the cleaved probe during sandwich hybridization allows its discrimination from un-cleaved probe for signal detection

ELECTROCHEMICAL POLYNUCLEOTIDE DETECTION COMPRISING LIGATION

CROSS-REFERENCE TO RELATED APPLICATION

This application claims priority from U.S. Provisional Application No. 60/748,998 filed on Dec. 9, 2005, which is incorporated herein by reference.

Disclosed, among other things, are methods comprising ligase-mediated capture of cleaved probe for electrochemical detection of nucleic acid amplicons.

Several isothermal nucleic acid amplification methods have been developed over the past decade as an alternative to the temperature cycling in PCR: HDA (Helicase Dependent Amplification); RCA (Rolling Circle Amplification); NASBA (Nucleic Acid Sequence Based Amplification); RAM (Ramification Amplification Method); LIDA (Logarithmic Isothermal DNA Amplification); TMA (Transcription-Mediated Amplification); LAMP (Loop-mediated isothermal Amplification); ICAN (Isothermal and Chimeric primer-initiated Amplification of Nucleic Acids); SDA (Strand Displacement Amplification), RPA (Recombinase-Polymerase Amplification) and several others. Among them SDA, RAM, RCA, ICAN (asymmetric variant), and three transcription-mediated methods such as NASBA (U.S. Pat. No. 5,130,238; U.S. Pat. No. 5,409,818; U.S. Pat. No. 5,554,517; U.S. Pat. No. 6,025,134), TMA (U.S. Pat. No. 5,399,491; U.S. Pat. No. 5,554,516; U.S. Pat. No. 5,766,849), LIDA (U.S. Pat. No. 6,531,300 B1; Pub. No.: US 2003/0050444 A1), generate a single-stranded RNA and/or DNA product during cycling reaction. This product can be potentially detected optically in real-time or end-point assay using product (amplicon)-specific complementary oligonucleotide probe, similar to fluorescently labeled probe such as TaqMan (cleavable probe), Molecular Beacon, Scorpion, and Cycling Probe (cleavable probe). This was reported so far only for real-time (and end-point) optical detection of NASBA (i.e. Leone et al., 1998; Landry et al., 2005) and RCA (Nilsson et al., 2002) with fluorescently labeled molecular beacons.

It is of interest to use cleavable probes for the real-time or end-point detection of amplicons generated during isothermal amplification methods mentioned above. If the probe consists of 1) a labeled portion (i.e. 5'-flap) homologous to the capture nucleic acid attached to the surface and amplicon specific 3' portion, and 2) labeled 5'-portion can be enzymatically cleaved off during hybridization of the probe to single-stranded amplicon, the detection scheme can be employed to detect the labeled 5'-portion of the probe on the surface upon it capture by capturing nucleic acid.

Thus, a need exists for improvements to real-time and end-point detection and quantification of target nucleic acid molecule (amplicons) using isothermal amplification methods.

The present disclosure is related to methods of capturing of cleavable portion on the surface, discriminating it from un-cleaved probe and of signal generation and detection.

The present disclosure provides novel approaches for discrimination between cleaved and un-cleaved electrochemically tagged probes (i.e. ferrocene-, osmium-tagged, etc.) and signal detection using electrochemistry. These approaches can be used for pathogene detection, monitoring specific gene expression, and other nucleic acid-based molecular diagnostic applications employing isothermal amplification methods such as, but not limited, to NASBA, LIDA, TMA, RPA, RAM, ICAN, LAMP, RCA.

The tagged portion of the probe can be cleaved by nucleic acid hydrolyses such as, but not limited, as DNA polymerases with 5'-3' exonuclease activity (Taq, Tth (HB-8, HB-27), Tma, Tne, Bst, Rob, Rma, and eubacterial PolA); structure-specific flap-endonucleases (*S. cerevisiae* Rad2, *S. pombe* Rad27, vertebrate XPG endonucleases, human FEN1, PfuFEN1, AfuFEN1); and Hollyday junction resolvases (eukaryotic Mus81/Mms4-Eme1 endonucleases, archaeal Hjc, metazoan XPF/ERCC1, yeast Rad1/Rad10 and Rad16/Swi10, yeast Slx1/Slx4).

A list of tags (labels) attached to the probe (preferably to the 5' end of the probe) includes, but is not limited by 1) biotin, 2) electrochemical tags (ferrocene, anthraquinone, osmium, etc.); 3) fluorescent molecules; 4) chromophors (luminescent or dye), and others.

A component of the method is the use of DNA (RNA) ligase capable of sealing the nick (or short gap). DNA/RNA ligase used in this method could be originating from mesophilic and thermophilic bacteria and phages, and metazoans such as, but not limited to T4 DNA ligase, Tth DNA ligase, Ampligase (Epicentre), Tsc and Ryna DNA ligases (Prokaria), Pfu DNA ligase (Stratagene), and Tfi DNA ligase (Hylabs). The key reaction is the ligase-mediated capture of cleaved tagged-portion of the probe on the surface by surface-bound capture nucleic acid molecule via hybridization. The capture nucleic acid is designed in a way that after annealing of cleaved labeled portion of the probe to capture (and bridging) probe the nick is generated in the formed duplex nucleic acid upon hybridization. This nick is immediately sealed by the action of thermostable or mesophilic DNA/RNA ligase ensuring stabilization of nucleic acid double-stranded hybrid.

Figure 2:
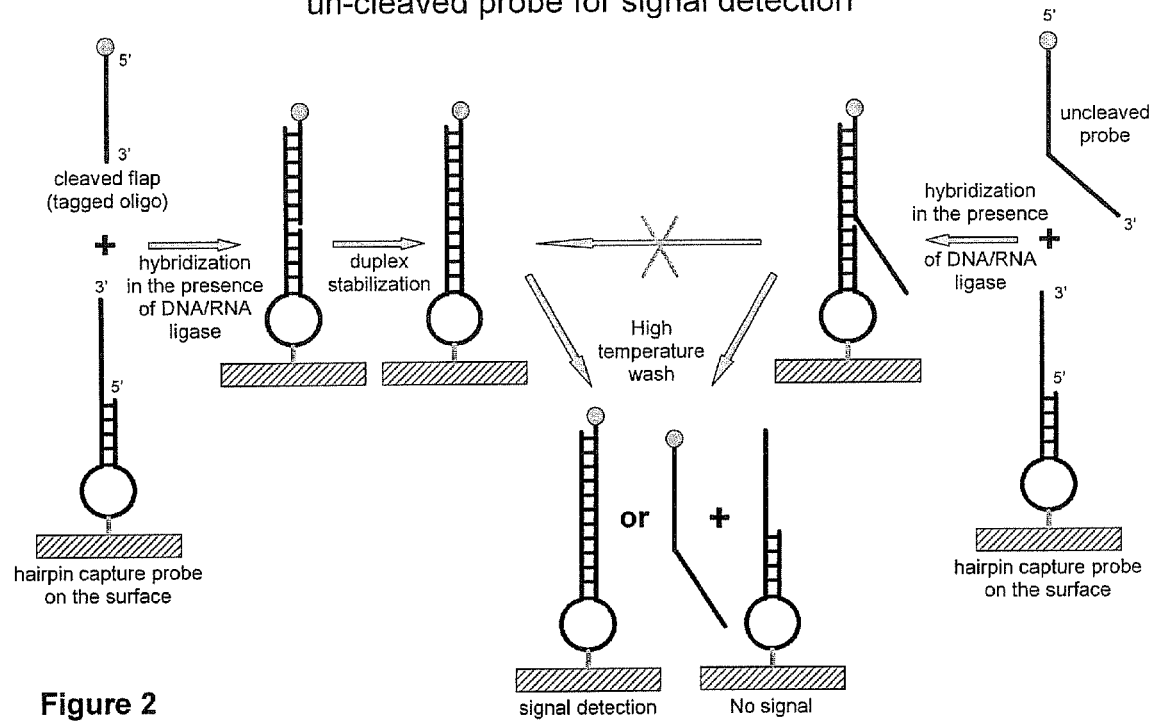

Two major strategy of ligase-mediated capture of the cleaved probe is proposed and depicted in FIG. 1 and FIG. 2.

A first strategy relates to sandwich hybridization of cleaved probe to the bridging oligonucleotide and surface-bound capture oligonucleotide. The resulting double-stranded nucleic acid structure is stabilized by the ligation of the nick. Uncleaved probe can not be stabilized by ligation because of the presence of the non-complementary 3'-flap. Upon the washing at raised temperature (above the Tm of the hybrid between un-cleaved probe and bridging oligonucleotide) the un-cleaved probe will be released and washed out, or not, if the detection will be performed at temperature higher than above mentioned T. This approach allows the discrimination between cleaved and un-cleaved probe for capturing at the surface and, thus, ensuring that only the cleaved probe can generation the signal (i.e. electrochemical). This results in low noise:background signal ratio.

A second strategy, uses a surface-bound hairpin capture probe (Lane et al., 1997; Ricccelli et al., 2001; U.S. Pat. No. 5,770,365) in conjunction with the use of nucleic acid ligase. In this approach cleaved probe is directly hybridized to hairpin capture probe forming a duplex structure with a nick (as depicted in FIG. 2). This nick is immediately sealed by nucleic acid ligase, thus the thering covalently the cleaved labeled to capture oligonucleotide and, thus to the surface. However, un-cleaved probe can not be covalently attached to the capture oligonucleotide via ligation reaction because of the 3'-flap bearing nucleotides non-complementary to capture probe at the 3-OH end. By increasing the temperature after certain time above the $T_m$ of unligated heteroduplex portion between labeled probe and capture probe only the cleaved (ligated) probe with attached label-tag will remain at the surface, thus, generating electrochemical signal, while un-cleaved probe could be washed away or precluded by high temperature to anneal to a capture probe. Periodic or endpoint electrochemical detection using voltammetric, potentiometric, or amperometric methods with or without an electrocatalytic substrate is used.

When other labeling tags are used in the cleavable probe (listed above) the corresponding detection method could be employed (colorimetric, luminescent etc.). Thus, the present invention claims the use of ligation-mediated capture of tagged cleavable probe useful for detection of amplicons in several isothermal amplification methods, which include:

i. stabilization of duplex at elevated temperatures by ligation of a nick between cleaved probe and capture probe strands, thus allowing discrimination between cleaved and un-cleaved probe.
ii. The use of hairpin capture probes in conjunction with ligation reaction.
iii. The use of sandwich hybridization approach in conjunction with ligation reaction for the purpose of increasing the duplex length and, thus, its stabilization at high temperatures.
iv. The use of all above mentioned in conjunction with electrochemical detection as specified above.

Potential Advantages

1. Simple method to discriminate/separate cleaved and un-cleaved labeled probe.
2. Stabilization of duplex formed by cleaved probe and capture (and bridging probe) by nucleic acid ligase allows the use of high temperature wash/flash to remove un-hybridized un-cleaved probe, thus increasing the signal:background ratio.

Exemplary Utilities

Bench-top, portable and handheld DNA detection devices/instrumentation (particularly, those employing hybridization/annealing of nucleic acid probe to the surface bound capture nucleic acid for electrochemical detection).

All references cited herein are hereby incorporated by reference in their entirety for all purposes.

REFERENCES

G. Leone, H. van Schijndel, B. van Gemen, F. R. Kramer, and C. D. Schoen (1998).
  Molecular beacon probes combined with amplification by NASBA enable homogeneous, real-time detection of RNA. Nucl. Acids. Res., v. 26, No. 9, pp. 2150-2155.
M. L. Landry, R. Garner, and D. Ferguson (2005) Real-time nucleic acid-based amplification using molecular beacons for detection of enterovirus RNA in clinical specimens. J. Clinical Microbial., v. 43, No 7, pp. 3136-3139.
M. Nilsson, M. Gullberg, F. Dahl, K. Szuhai, and A. K. Raap (2002) Real-time monitoring of rolling-circle amplification using a modified molecular beacon design. Nucl. Acids Res., V. 30, No. 14, e66.
M. J. Lane, T. Paner, I. Kashin, B. D. Faldaz, L. B. Gallo, A. S. Benight (1997) The thermodynamic advantage of DNA oligonucleotide "stacking hybridization" reactions: energetic sod a DNA nick. Nucl. Acids Res., v. 25, No. 3, pp. 611-617.
P. V. Riccelli, F. Merante, K. T. Leung, S. Bortolin, R. L. Zastawny, R. Janeczko, and A. S. Benight (2001), Hybridization of single-stranded DNA targets to immobilize complementary DNA probes: comparison of hairpin versus linear capture probes, Nucl. Acids Res., v. 29, No. 4, pp. 996-1004.

DESCRIPTIONS OF DRAWINGS

FIG. 1 illustrates an assay format in which a flap 1 that has been cleaved from a probe (uncleaved probe) hybridizes with a bridging oligonucleotide 2 that is hybridized to a capture oligonucleotide 3 on a surface to form a hybridization complex in which abutting ends (3' and 5', or 5' and 3') of flap 1 and capture oligonucleotide 3, respectively, are hybridized immediately adjacent to each other so as to be ligatable by a ligase. Ligation of the abutting ends of flap 1 and oligonucleotide 3 by the ligase forms a ligation product that remains captured on the support. Non-ligated uncleaved probe can be removed by washing if desired. The immobilized ligation product can be detected directly or using a detectable label provided by ligated flap 1. On the other hand, although the flap segment in an uncleaved probe may hybridize to bridging oligonucleotide 2, the uncleaved probe is incapable of being ligated to the capture probe due to the presence of an additional 3' sequence segment that is not complementary to the bridging oligonucleotide. (Although the figure shows an uncleaved probe labeled at the 5' end and having a non-ligatable 3' end, the 5'-3' polarity of moieties 1, 2 and 3 can be reversed such that a 5' end of a flap becomes ligated to a 3' end of a capture oligonucleotide.

FIG. 2 illustrates an assay format in which a capture probe is provided as a duplex containing a sticky end such that a protruding strand can serve as a bridging oligonucleotide (analogous to the format in FIG. 1) for hybridizing with a cleaved flap to form a hybridization complex, followed by ligation of one end (3' end in the figure) of the cleaved flap to an abutting end (5' in the figure) of a recessed strand to form a ligated product that is then detected. Although the capture probe in FIG. 2 is illustrated as a hairpin, if may also be provided in a non-hairpin hybridization complex pre-formed on the surface, for hybridization with and ligation to a cleaved flap.

The invention claimed is:

1. A nucleic acid detection method comprising:
  cleaving a portion of labeled probes in an isothermal amplification process to form a labeled cleaved oligonucleotide probe and a labeled uncleaved oligonucleotide probe, wherein the labeled cleaved oligonucleotide probe consists of a labeled cleaved oligonucleotide flap and an electrochemical label attached thereto, and the uncleaved oligonucleotide probe consists of an uncleaved oligonucleotide flap and an electrochemical label attached thereto;
  forming a first nucleic acid double-stranded structure between the labeled cleaved oligonucleotide flap of the labeled cleaved oligonucleotide probe, a bridging oligonucleotide, and a capture oligonucleotide that is immobilized on a surface, such that the labeled cleaved oligonucleotide flap and the capture oligonucleotide are hybridized to immediately adjacent, complementary regions of the bridging oligonucleotide;
  contacting a ligase with the first nucleic acid double-stranded structure;
  detecting, in real time, the first nucleic acid double-stranded structure during the isothermal amplification process by electrochemically detecting the electrochemical label of the labeled cleaved oligonucleotide probe by using a method selected from voltammetric methods, potentiometric methods, amperometric methods, and combinations thereof,
  wherein the isothermal amplification process is selected from the group consisting of Helicase Dependent Amplification, Rolling Circle Amplification, Nucleic Acid Sequence Based Amplification, Ramification Amplification Method, Logarithmic Isothermal DNA Amplification, Transcription-Mediated Amplification, Loop-mediated Isothermal Amplification, Isothermal and Chimeric Primer-Initiated Amplification of Nucleic Acids, Strand Displacement Amplification, and Recombinase-Polymerase Amplification; and forming a second nucleic acid double-stranded structure between a labeled uncleaved oligonucleotide flap, a bridging oligonucleotide, and a capture oligonucleotide that is immobilized on a surface, such that the labeled uncleaved oligonucleotide flap and the capture oligonucleotide are hybridized to immediately adjacent, complimentary regions of the bridging oligonucleotide, wherein the first and second nucleic acid double stranded structures are washed at a temperature greater than the melting temperature of the second nucleic acid double stranded structure.

2. The method of claim 1, wherein the bridging oligonucleotide and the capture oligonucleotide are contained in a hairpin structure.

3. The method of claim 1, wherein the electrochemical label is selected from ferrocene labels, osmium labels, anthraquinone labels, and combinations thereof.

\* \* \* \* \*